United States Patent
Huang et al.

(10) Patent No.: US 10,172,945 B2
(45) Date of Patent: Jan. 8, 2019

(54) SORBITAN POLYESTER CONJUGATES FOR STABILIZING WATER-IN-OIL EMULSIONS AND DELIVERING CONTROLLED RELEASE OF BIOACTIVE AGENTS

(71) Applicant: NATIONAL HEALTH RESEARCH INSTITUTES, Miaoli County (TW)

(72) Inventors: Ming-Hsi Huang, Miaoli County (TW); Chiung-Yi Huang, Miaoli County (TW); Pele Choi-Sing Chong, Miaoli County (TW); Chih-Hsiang Leng, Miaoli County (TW); Shih-Jen Liu, Miaoli County (TW); Hsin-Wei Chen, Miaoli County (TW)

(73) Assignee: NATIONAL HEALTH RESEARCH INSTITUTES, Miaoli County (TW)

( * ) Notice: Subject to any disclaimer, the term of this patent is extended or adjusted under 35 U.S.C. 154(b) by 0 days.

(21) Appl. No.: 15/547,490

(22) PCT Filed: Jan. 12, 2016

(86) PCT No.: PCT/US2016/012943
§ 371 (c)(1),
(2) Date: Jul. 29, 2017

(87) PCT Pub. No.: WO2016/126387
PCT Pub. Date: Aug. 11, 2016

(65) Prior Publication Data
US 2018/0008713 A1    Jan. 11, 2018

Related U.S. Application Data

(60) Provisional application No. 62/112,154, filed on Feb. 4, 2015.

(51) Int. Cl.
| | |
|---|---|
| *A61K 47/34* | (2017.01) |
| *A61K 39/39* | (2006.01) |
| *A61K 47/06* | (2006.01) |
| *C08G 63/672* | (2006.01) |
| *A61K 9/113* | (2006.01) |
| *C08G 65/332* | (2006.01) |
| *A61K 39/00* | (2006.01) |
| *A61K 9/00* | (2006.01) |

(52) U.S. Cl.
CPC ............ *A61K 47/34* (2013.01); *A61K 9/0019* (2013.01); *A61K 9/113* (2013.01); *A61K 39/00* (2013.01); *A61K 39/39* (2013.01); *A61K 47/06* (2013.01); *C08G 63/672* (2013.01); *C08G 65/3328* (2013.01); *A61K 2039/55555* (2013.01); *A61K 2039/55566* (2013.01); *C08G 2650/02* (2013.01)

(58) Field of Classification Search
None
See application file for complete search history.

(56) References Cited

U.S. PATENT DOCUMENTS 8,444,993 B2    5/2013    Huang et al.

OTHER PUBLICATIONS

Huang et al. (2010) Emulsified Nanoparticles Containing Inactivated Influenza Virus and CpG Oligodeoxynucleotides Critically Influences the Host Immune Responses in Mice. PLoS One 5(8): e12279. doi:10.1371/journal.pone.0012279.
Chang et al. (2013) Enzymatic Stability and Immunoregulatory Efficacy of a Synthetic Indolicidin Analogue with Regular Enantiomeric Sequence. ACS Med. Chem. Lett. 4: 522-526.
Dietmar W. Hutmacher (2000) Scalolds in tissue engineering bore and cartilage. Biomaterials 21; 2529-2543.

*Primary Examiner* — Nicole P Babson
(74) *Attorney, Agent, or Firm* — Hsiu-Ming Saunders; Intellectual Property Connections Inc.

(57) ABSTRACT

A composition in a water-in-oil-in-water (W/O/W) emulsion is disclosed. The composition comprises: (a) a continuous aqueous phase, comprising $H_2O$; (b) an oil phase or an oil shell, dispersed in the continuous aqueous phase; and (c) a hydrophilic polymer, stabilizing an interface between the continuous aqueous phase and the oil phase or the oil shell to form the water-in-oil-in-water (W/O/W) emulsion. The oil phase or the oil shell comprises: (i) oil; (ii) an internal aqueous phase, dispersed within the oil or the oil shell; and (iii) a lipophilic sorbitan-polyester conjugate, stabilizing an interface between the oil and the inner aqueous phase to form a water-in-oil (W/O) emulsion. The lipophilic sorbitan-polyester conjugate comprises: (1) sorbitan; and (2) poly (lactide-co-ε-caprolactone) or polylactic acid (polylactide), conjugated to the sorbitan.

20 Claims, 4 Drawing Sheets
Specification includes a Sequence Listing.

Time after single-dose injection (weeks)

PBS/squalene/sorbitan-PLACL/PEG-b-PLACL

FIG. 6C

PBS/squalene/SPAN®85/TWEEN®80

FIG. 6D

PBS/squalene/SPAN®85/PEG-b-PLACL

```
                    SEQUENCE LISTING

<160> NUMBER OF SEQ ID NOS: 1

<210> SEQ ID NO 1
<211> LENGTH: 13
<212> TYPE: PRT
<213> ORGANISM: bovine

<400> SEQUENCE: 1

Ile Leu Pro Trp Lys Trp Pro Trp Trp Pro Trp Arg Arg
1               5                   10
```

SORBITAN POLYESTER CONJUGATES FOR STABILIZING WATER-IN-OIL EMULSIONS AND DELIVERING CONTROLLED RELEASE OF BIOACTIVE AGENTS

REFERENCE TO RELATED APPLICATION

This application is a national stage application (under 35 U.S.C. 371) of PCT/US2016/012943 filed on 12 Jan. 2016, which claims priority to U.S. provisional application 62/112,154 filed on 4 Feb. 2015, all of which are, herein incorporated by reference in their entireties.

FIELD OF THE INVENTION

The present invention relates generally to water-oil-in-water (W/O/W) double emulsions, especially relates to emulsifiers for use in preparation of W/O/W double emulsions.

BACKGROUND OF THE INVENTION

Water-in-oil-in-water double emulsions are systems in which a water-in-oil (W/O) emulsion is dispersed in a second aqueous phase. The W/O emulsion exists in the suspending aqueous medium as oil globules containing smaller water droplets. Preparation of W/O/W emulsions requires an emulsifying system with an intermediate HLB (hydrophilic-lipophilic balance) value. A W/O emulsion is first prepared using a lipophilic emulsifier such as SPAN® 85, while during the second step, the W/O emulsion was mixed with an aqueous solution of a hydrophilic emulsifier such as TWEEN® 80 to provide W/O/W emulsions. Two key challenges in vaccine development are related to developing formulations that do not require refrigeration and finding an absorbable adjuvant in vivo. The former maintains and preserves the quality of a vaccine before it is administered, and the latter is critical to evading hypersensitive reactions after vaccine administration.

U.S. Pat. No. 8,444,993 discloses a W/O/W emulsion comprising SPAN® 85 and poly(ethylene glycol)-block-poly(lactide-co-ε-caprolactone) (PEG-b-PLACL) as an emulsifying agent. That emulsion system exhibited a controlled release of antigen similar to SPAN/TWEEN emulsion. However for a W/O/W emulsion, having the same controlled release effect does not translate into having the same emulsion-stabilizing effect (see FIGS. 6C and 6D). Moreover, it has been well documented that the traditional emulsifiers TWEEN®, SPAN® and poloxamers may cause toxicities including severe nonimmunological anaphylactoid reactions.

A heretofore unaddressed need exists in the art to address the aforementioned deficiencies and inadequacies, especially in connection with formulations of W/O/W emulsions that are biodegradable without using sorbitan esters and their ethoxylates (SPAN® and TWEEN®), or poloxamers.

SUMMARY OF THE INVENTION

In one aspect, the invention relates to a composition in a water-in-oil-in-water (W/O/W) emulsion, comprising:
(a) a continuous aqueous phase, comprising $H_2O$; and
(b) an oil phase or an oil shell, dispersed in the continuous aqueous phase, the oil phase or the oil shell comprising:
  (i) oil;
  (ii) an internal aqueous phase, dispersed within the oil or the oil shell; and
  (iii) a lipophilic sorbitan-polyester conjugate, stabilizing an interface between the oil and the inner aqueous phase to form a water-in-oil (W/O) emulsion, the lipophilic sorbitan-polyester conjugate comprising:
    (1) sorbitan; and
    (2) poly(lactide-co-ε-caprolactone) or polylactic acid (polylactide), conjugated to the sorbitan; and
(c) a hydrophilic polymer, stabilizing an interface between the continuous aqueous phase and the oil phase or the oil shell to form an oil-in-water (O/W) emulsion.

In one embodiment of the invention, the weight ratio of sorbitan:lactide:caprolactone in the sorbitan-poly(lactide-co-ε-caprolactone) conjugate is greater than 1:2:2 but less than 1:12:12.

In another embodiment of the invention, the weight ratio of sorbitan:lactide:caprolactone in the sorbitan-poly(lactide-co-ε-caprolactone) conjugate ranges from 1:3:3 to 1:8:8.

In another embodiment of the invention, the hydrophilic polymer is selected from the group consisting of poly(ethylene glycol)-block-poly(lactide-co-ε-caprolactone) and poly(ethylene glycol)-block-polylactide.

In another embodiment of the invention, the inner aqueous phase or the continuous aqueous phase comprises an antigen or a bioactive agent.

In another embodiment of the invention, the bioactive agent is an immunostimulant.

In another embodiment of the invention, the continuous aqueous phase may comprise an antigen and the inner aqueous phase may comprise a bioactive agent, or vice versa.

In another embodiment of the invention, the oil phase or the oil shell has a particle size ranging from 400 to 600 nm.

A composition in a W/O/W emulsion as aforementioned is free of sorbitan esters, sorbitan ethoxylates, esters of fatty acids and hexitol anhydrides, mannide monooleate, or poloxamers.

In another aspect, the invention relates to a method of preparing a composition in a water-in-oil-in water (W/O/W) emulsion as aforementioned, which comprises the following steps:
(a) introducing sorbitan, monomethoxy polyethylene glycol, DL-lactide into a reactor;
(b) performing a polymerization of the DL-lactide on the sorbitan and the monomethoxy polyethylene glycol in the presence of a catalyst to afford a mixture containing sorbitan-polylactide conjugate and poly(ethylene glycol)-block-polylactide;
(c) dissolving the mixture containing the sorbitan-polylactide conjugate and the poly(ethylene glycol)-block-polylactide in a first aqueous solution, which optionally comprises an antigen or a bioactive agent, to obtain a first aqueous mixture;
(d) admixing the first aqueous mixture with oil to obtain an aqueous oil mixture; and
(e) homogenizing the aqueous oil mixture to afford the composition in a W/O/W emulsion as aforementioned.

Alternatively, a method of preparing a composition in a water-in-oil-in water (W/O/W) emulsion as aforementioned comprises the following steps:
(i) performing an anhydrization reaction of sorbitol in the presence of phosphoric acid to afford sorbitan; and
(ii) admixing the sorbitan with DL-lactide and ε-caprolactone and performing a polymerization reaction of the DL-lactide and the ε-caprolactone on the sorbitan to afford the sorbitan-polyester conjugate;

(iii) dissolving the sorbitan-polyester conjugate and poly(ethylene glycol)-block-poly(lactide-co-ε-caprolactone) in a first aqueous solution, which optionally comprises an antigen or a bioactive agent, to obtain a first aqueous mixture;
(iv) admixing the first aqueous mixture with oil to obtain an aqueous oil mixture; and
(v) homogenizing the aqueous oil mixture to afford the composition in a W/O/W emulsion as aforementioned.

The method as aforementioned may further comprises:
(i) providing a second aqueous solution comprising an antigen or a bioactive agent with the proviso that the first aqueous solution does not comprise the antigen or the bioactive agent; and
(ii) dispersing the composition in a W/O/W emulsion from step (e) or (v) into the second aqueous solution comprising the antigen or the bioactive agent to afford the composition in a W/O/W emulsion with the antigen or the bioactive agent adsorbed on the oil phase or on the oil shell.

The first aqueous solution in the aforementioned method may comprise an antigen or a bioactive agent to afford a composition in a W/O/W emulsion as aforementioned with the antigen or the bioactive agent encapsulated within the oil phase or within the oil shell.

In another aspect, the invention relates to use of a composition in a water-in-oil-in water (W/O/W) emulsion as aforementioned in the manufacture of a medicament for enhancing a body's response to an immunogen, for delivering an immunogen or a bioactive agent into a body, and/or for inducing activation and/or maturation of an antigen presenting cell, in a subject in need thereof.

These and other aspects will become apparent from the following description of the preferred embodiment taken in conjunction with the following drawings, although variations and modifications therein may be affected without departing from the spirit and scope of the novel concepts of the disclosure. The accompanying drawings illustrate one or more embodiments of the invention and, together with the written description, serve to explain the principles of the invention. Wherever possible, the same reference numbers are used throughout the drawings to refer to the same or like elements of an embodiment.

DETAILED DESCRIPTION OF THE INVENTION

DEFINITIONS

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

Sorbitan-PLACL conjugate 1:2:2 shall generally mean the weight ratio of sorbitan:lactide:caprolactone is 1:2:2; Sorbitan-PLACL conjugate 1:4:4 shall mean the weight ratio of sorbitan:lactide:caprolactone is 1:4:4; sorbitan-PLACL 1:8:8 shall mean sorbitan:lactide:caprolactone weight ratio is 1:8:8; sorbitan-PLACL 1:12:12 shall mean sorbitan:lactide:caprolactone weight ratio is 1:12:12; sorbitol-PLACL 1:4:4 shall mean sorbitol:lactide:caprolactone weight ratio is 1:4:4.

The term "polysorbasome encapsulation" refers to a polysorbasome-formulated vaccine composition comprising an antigen or a bioactive agent encapsulated within the oil or the oil shell of the polysorbasome. It is prepared by introducing the antigen and/or the bioactive agent into the first phosphate buffered saline (PBS-1) aqueous solution (FIG. 2B).

The term "polysorbasome adsorption" refers to a polysorbasome-formulated vaccine composition comprising an antigen or a bioactive agent adsorbed onto the surface of the polysorbasome. It is prepared by introducing the antigen and/or the bioactive agent into the second phosphate buffered saline (PBS-2) aqueous solution (FIG. 2B).

Immunostimulants, also known as immunostimulators, are substances (drugs and nutrients) that stimulate the immune system by inducing activation or increasing activity of any of its components. Examples of immunostimulants include, but are not limited to, toll-like receptor (TLR) agonists such as CpG oligodeoxynucleotides (TLR-9) and host defense peptides (TLR-4), saponins (TLR-2, TLR-4), monophosphoryl lipid A (TLR-4), and flagellin (TLR-5).

Bioactive agents include, but are not limited to, antigens, immunostimulants, CpG oligodeoxynucleotides, and host defense peptide analogues. For example, an analogue, dubbed LD-indolicidin, contains a regular enantiomeric sequence of indolicidin (ILPWKWPWWPWRR-$NH_2$; SEQ ID NO: 1) (Huang et al. "Emulsified Nanoparticles Containing Inactivated Influenza Virus and CpG Oligodeoxynucleotides Critically Influences the Host Immune Responses in Mice" PLoS ONE 2010, vol 5, issue 8, e12279; Chang et al. "Enzymatic Stability and Immunoregulatory Efficacy of a Synthetic Indolicidin Analogue with Regular Enantiomeric Sequence" ACS Medicinal Chemistry Letters 2013, 4, 522-526).

As used herein, "immunity adjuvants" shall generally mean products which increase the reactions of the immunity system when they are administered in the presence of antigen of virus, bacterial or synthetic origin.

As used herein, the term "biodegradable" shall generally mean solid polymeric materials which break down due to macromolecular degradation with dispersion in vivo but no proof for the elimination from the body (this definition excludes environmental, fungi or bacterial degradation). Biodegradable polymeric systems can be attacked by biological elements so that the integrity of the system, and in some cases but not necessarily, of the macromolecules themselves is affected and gives fragments or other degradation by-products. Such fragments can move away from their site of action but not necessarily from the body.

As used herein, the term "bioresorbable" shall generally mean solid polymeric materials which show bulk degradation and further resorb in vivo; i.e. polymers which are eliminated through natural pathways either because of simple filtration of degradation by-products or after their metabolization. Bioresorption is thus a concept which reflects a total elimination of the initial foreign material and of bulk degradation by-products (low molecular weight compounds) with no residual side effects. The use of the word 'bioresorbable' assumes that the elimination is shown conclusively (Dietmar W. Hutmacher (2000) "Scaffolds in tissue engineering bone and cartilage" Biomaterials 21:2529-2543, which is herein incorporated by reference in its entirety).

As used herein, a "lactone" is a cyclic ester which can be seen as the condensation product of an alcohol group —OH and a carboxylic acid group —COOH in the same molecule. It is characterized by a closed ring consisting of two or more carbon atoms and a single oxygen atom, with a ketone group =O in one of the carbons adjacent to the latter. A "lactide" is a cyclic diester of lactic acid, i.e., a di-lactone. A "glycolide" is a cyclic diester of glycolic acid, which is also a di-lactone.

Emulsifiers may be defined by their hydrophilic-lipophilic balance (HLB) values, which give information on their relative affinity for aqueous and oily phases. An emulsifying system which contains an emulsifier of low HLB value renders a W/O emulsion with a high affinity for an oily phase. In contrast, an emulsifying system which contains a high HLB value affords an O/W emulsion with a high affinity for an aqueous phase. A W/O/W multi-phase emulsion may be achieved when an emulsifying system contains an intermediate HLB value. These parameters, however, are strongly influenced by the optimization of a surfactant system and the manufacture process.

For an emulsifier system comprising one or more emulsifiers, the HLB is calculated based on the following equation:

$$HLB_{mix} = \Sigma X_i \times HLB_i$$

where X is the weight fraction of surfactant i.

For non-ionic surfactants, HLB may be calculated with the Griffin's method:

$$HLB = 20 \times M_h / M$$

where $M_h$ is the molecular mass of the hydrophilic portion of the molecule, and M is the molecular mass of the whole molecule. The HLB of the most lipophilic molecule is close to 0, while the HLB of the most hydrophilic molecule is about 20.

For a non-ionic copolymer, the equation can be represented as follows:

$$HLB_{copolymer} = 20 \times W_h / W_{copolymer}$$

where $W_h/W_{copolymer}$ is the weight ratio of the hydrophilic portion of the main chain polymer and is obtained from their number average molecular weight ratio $\overline{Mn}_h/\overline{Mn}_{copolymer}$.

A W/O emulsion based on lipophilic mannide monooleate and water-immiscible oil has been available. The oil used is the mineral oil Markol (Freund's adjuvants), metabolizable mineral oil Drakeol (MONTANIDE® ISA 51) or metabolizable nonmineral squalene (MONTANIDE® ISA 720). TITERMAX® is a squalene-based W/O emulsion stabilized by microparticulate silica and the nonionic block copolymer polyoxyethylene-polyoxypropylene-polyoxyethylene (POE-POP-POE, known as PLURONIC® or poloxamer). These W/O emulsions are difficult for injection with a syringe having a needle of small diameters, and cause local reactions at the injection site of animals, which considerably restrained the potential of this type of emulsions for human use.

The invention relates to sorbitan-polyester conjugates for use as a lipophilic emulsifier rather than using SPAN®, poloxamers (also known by trade names SYNPERNONICS™, PLURONICS™, KOLLIPHOR™), or mannide monooleate. Sorbitan-polyester conjugates was prepared by first making sorbitan (anhydro-sorbitol) via phosphoric acid-catalyzed anhydrization, then reacting the sorbitan with DL-lactide and -caprolactone in the presence of $SnOct_2$ at 140° C. for 24 hr. The sorbitan-PLACL conjugates are composed of hydrophilic sorbitan moiety and lipophilic block PLACL. The sorbitan-PLACL conjugate was used in combination with PEG-b-PLACL as emulsifier components to stabilize oil/water interfaces, rendering multiphase oil-shelled capsules contain an aqueous solution in the core and provide an oily barrier that isolates the encapsulated material from the external materials. The emulsion of the invention does not contain poloxamers.

The invention relates to the discovery that sorbitan-PLACL conjugate as an emulsification agent can stabilize aqueous/oily interfaces. The emulsified vaccine delivery systems (dubbed polysorbasomes) have several advantages over traditional emulsions. First, the oil-shelled capsules are useful for encapsulating and protecting designed bioactive molecules. Second. both polylactide (PLA) and polycaprolactone (PCL) are biodegradable polyesters, the loss of poly(lactide-co-ε-caprolactone), i.e., PLACL, moiety of the emulsifiers PEGylated polyesters/sorbitan-polyesters directly affected the stability of the emulsion, leading to phase separation of oil/water and hydrolysis-triggered controlled release. Another advantage of polysorbasomes is its internalization by APCs probably via receptor-mediated endocytosis and phagocytosis, which may facilitate induction of cell-mediated immunity.

The invention relates to the discovery of the bioresorbable polymers PEGylated polyesters/sorbitan-polyesters as a promising strategy for delivery of vaccine antigens and/or immunostimulatory molecules. The polysorbasome (polymeric resorbable vehicle) of the invention allows stabilization of emulsified particles during storage, but allows disintegration of the particles post-injection. All the components show main chain cleavage into small molecules and further absorption in vivo.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Preparation of a PEGylated-Polyester Copolymer

PEG-b-PLACL was synthesized by ring-opening polymerization of lactide and ε-caprolactone, using $SnOct_2$ as a catalyst and $MePEG_{5000}$ as an initiator. Briefly, predetermined amount of $MePEG_{5000}$ (2.1 g), lactide (0.58 g), and ε-caprolactone (0.47 g) were placed into a polymerization ampoule. The mixture was further degassed and sealed under vacuum. Polymerization was carried out in bulk under vacuum at 140° C. for 24 hours. The copolymer was dissolved in acetone and then poured in ethanol. The precipitated polymer was finally collected by filtration and dried in vacuo to yield pure product.

Preparation of a Sorbitan-Polyester Conjugate

Synthesis of sorbitan-polyester conjugates was conducted by two-stage method. Firstly, a predetermined amount of sorbitol was fed to the flask. Preparation of sorbitan was simply by distilling water out of sorbitol at 180° C. for 2 hr in the presence of phosphoric acid, using a system composed of ROTAVAPOR® R-210 (Buchi Labortechnik AG, Switzerland) under vacuum. In the second stage, the sorbitan-polyester conjugate was synthesized by ring-opening polymerization of DL-lactide (13.92 g) and ε-caprolactone (13.92 g) in the presence of sorbitan (3.48 g) and $SnOct_2$ (155 μL) at 140° C. for 24 hr. The resulting sorbitan-poly (DL-lactide-co-s-caprolactone) conjugate (sorbitan-PLACL 1:4:4) was dissolved in 100 ml of dichloromethane, and then the solution was washed with 50 ml of distilled water, the solvent of the organic phase will be partially evaporated under reduced pressure. The resulting polymers were characterized by gel permeation chromatography (GPC) and mass spectroscopy.

Figure 1A:
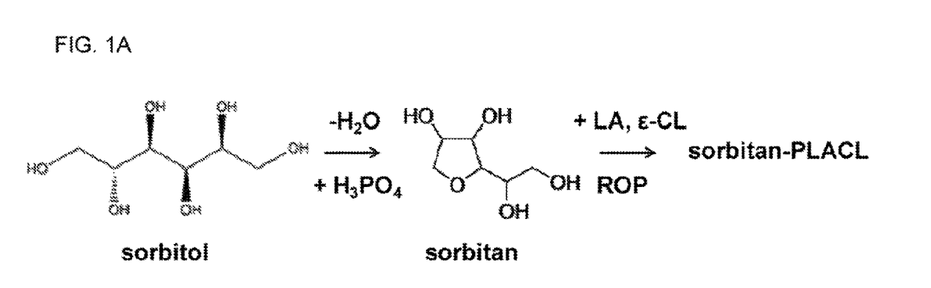
FIG. 1A is a schematic drawing showing preparation of a sorbitan-polyester conjugate.

FIG. 1A shows a synthesis scheme of a sorbitan-polyester conjugate. Sorbitan was prepared by phosphoric acid-catalyzed anhydrization. Sorbitan-PLACL conjugate was then synthesized by polymerization of DL-lactide and ε-caprolactone on sorbitan. The sorbitan-PLACL conjugate composes of hydrophilic sorbitan moiety and lipophilic PLACL segment. Phosphoric acid was selected as the catalyst because it catalyses the conversion of sorbitol to sorbitan in a high yield, and the subsequent dehydration to isosorbide proceeds at a significantly low rate, compared to conventional catalyst p-toluene-sulphonic acid. The term "PLACL" stands for poly(lactide-co-ε-caprolactone).

Figure 1B:
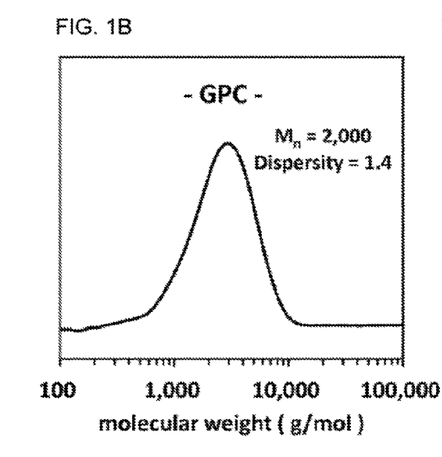
FIGS. 1B-C show the results of sorbitan-polyester conjugates using gel permeation chromatography (GPC) and matrix-assisted laser desorption/ionization (MALDI) analyses, respectively.

FIG. 1B shows GPC traces of sorbitan-PLACL conjugate. The sorbitan-PLACL exhibited a single peak with a narrow molecular weight distribution, indicating the absence of non-reacted DL-lactide and ε-caprolactone. The mean of MW is about 2000 g/mole with a dispersity of about 1.4.

Figure 1C:
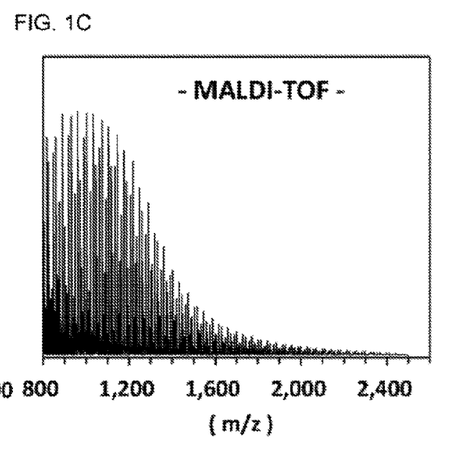

FIG. 1C shows MALDI-TOF mass spectrometry for measuring the detail molecular weight of the sorbitan-PLACL conjugate. The sorbitan-PLACL spectra were well resolved, and the peaks were separated by 114 and 72 mass units, which corresponded to the molecular weight of the CL monomer (caproyl units=114.14 g/mol) and LA motif (lactyl units=72.06 g/mol), respectively. The molecular weight of sorbitan-PLACL conjugate ranged from 800 to 2400 g/mol. The term "LA" stands for lactide. The term CL stands for "caprolactone".

Polysorbasome Preparation

We investigated the sorbitan-PLACL conjugate as an emulsification agent for stabilizing aqueous/oily interfaces. The sorbitan-polyester conjugate was used as a lipophilic emulsifier and PEG-b-PLACL as a hydrophilic emulsifier, yielding emulsified polysorbasome. 120 mg of PEG-b-PLACL, 120 mg of sorbitan-PLACL, 0.8 mL of antigen medium and 0.9 mL of squalene oil were emulsified using POLYTRON® PT 3100 homogeniser (Kinematica AG, Swiss) under 6,000 rpm for 5 min. The emulsified formulation served as stock for further physicochemical characterizations named stability, the droplet test, and particle size distribution.

Figure 2A:
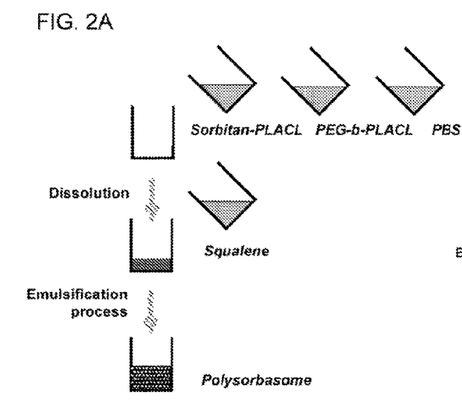
FIGS. 2A-B are schematic drawings showing preparation of polysorbasonie and polysorbasome-formulated vaccine compositions.
Figure 2B:
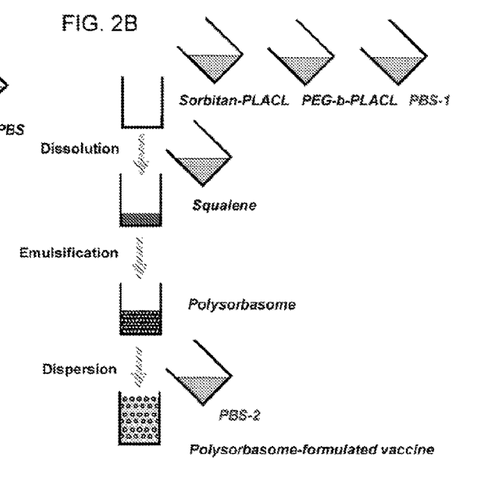
Figure 3A:
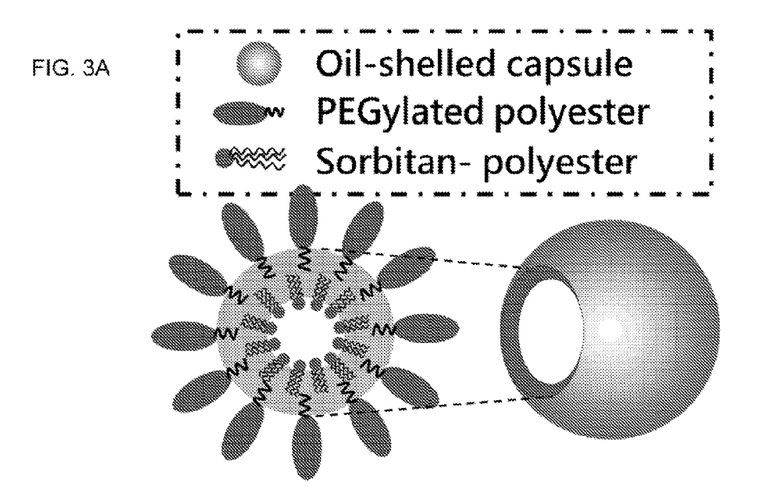
FIG. 3A is a schematic drawing illustrating a water-in-oil-in-water (W/O/W) polysorbasome.

FIG.2A illustrates preparation of polysorbasome. PEG-b-PLACL and sorbitan-PLACL are dissolved in. PBS, followed by mixing with squalene oil and homogenization to result in polysorbasome (FIG. 3A). Squalene was selected as the core oil because it is a human natural metabolite, the precursor of cholesterol, and therefore of vitamin .D and many hormones. FIG. 2B illustrates preparation of polysorbasome with an antigen or a bioactive agent being encapsulated and/or adsorbed on the oil phase or the oil shell of the polysorbasome. An antigen or a bioactive agent may be present in the first phosphate-buffered saline aqueous solution to prepare a polysorbasome-formulated vaccine or medicament with the antigen or the bioactive agent being encapsulated and adsorbed on the oil phase or the oil shell. Alternatively, the antigen or the bioactive agent may be present only in the second phosphate-buffered saline aqueous solution to prepare a polysorbasome-formulated vaccine or medicament with the antigen or the bioactive agent being adsorbed on the oil phase or the oil shell. In some instances, the first phosphate-buffered saline aqueous solution may contain an antigen and the second phosphate-buffered saline aqueous solution may contain a bioactive agent, or vice versa, to prepare a polysorbasome-formulated vaccine or medicament with the antigen being encapsulated within and the bioactive agent being adsorbed on the oil phase or the oil shell, or with the antigen being adsorbed on and the bioactive agent being encapsulated within the oil phase or the oil shell.

Figure 3B:
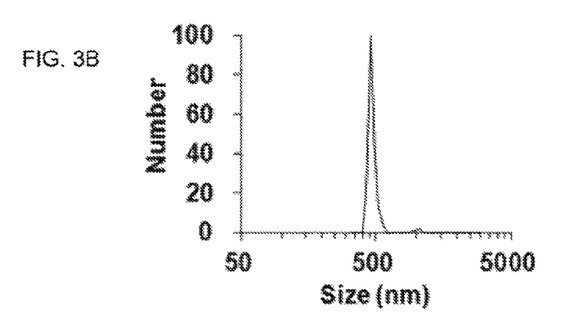
FIG. 3B shows the result of a laser light scattering analysis of a polysorbasome comprising BSA/PBS/PEG-b-PLACL/squalene/sorbitan-PLACL 1:4:4. BSA stands for bovine serum albumin.

The dispersion-type of emulsion was investigated by droplet test and light scattering analysis. The droplet test was assessed with a droplet (20 µL) of emulsion into a water containing beaker (200 mL). The particle size distribution was determined by the laser light scattering technique using a Brookhaven 90 plus particle sizer (Brookhaven Instruments Limited, New York). PEG-b-PLACL and sorbitan-PLACL stabilized squalene droplet can stand only for seconds in aqueous solution and then diffuses in the water, indicating a continuous phase of water. Dynamic light scattering showed that the emulsified particles possess a unimodal distribution with the diameter of 400-600 nm (FIG. 3B). The particle size of emulsions has poor reproducibility because it depends on factors such as storage duration, PBS/squalene ratio or the ratio of PEG-b-PLACL/sorbitan-PLACL or processing procedures, etc., all of which have impacts on the particle size of emulsions. Laser light scattering analysis and in vitro release data showed that PEG-b-PLACL/squalene/sorbitan-PLACL is composed of two emulsifiers and renders a water-in-oil-in-water (W/O/W) multiphase emulsion (FIG. 3A).

Effects of Vaccine's Components on Controlled Release

The antigen medium was prepared with a particular concentration of bovine serum albumin (BSA) diluted in PBS. Three formulations were prepared as follows:
(1) 120 mg of PEG-b-PLACL, 0.8 mL of antigen medium and 1.08 mL of squalene oil (O/W);
(2) 120 mg of PEG-b-PLACL, 0.8 mL of antigen medium and 1.08 mL of oil solution (squalene/SPAN®85 with 85/15 v/v; W/O/W);
(3) 120 mg of PEG-b-PLACL, 120 mg of sorbitan-PLACL, 0.8 mL of antigen medium and 0.96 mL of squalene oil (W/O/W);

The mixtures were emulsified using a POLYTRON® PT 3100 homogeniser (Kinematica AG, Swiss) under 6,000 rpm for 5 min.

In vitro release experiments were performed by using the inverted dialysis tube method. BSA-containing formulations (3 mg per 0.3 mL) were first placed in a dialysis chamber (cut-off 0.2 µm) and then the chamber was immersed in a 50 mL centrifuge tube containing 2 mL of PBS at 37° C. At different time intervals, 100 µL of sample were aspirated from the medium outside of the chamber and then replaced with 100 µL of PBS buffer. The BSA release was regularly determined by bicinchoninic acid method (BCA™ protein assay kit, Pierce, Rockford, Ill.).

Figure 3C:
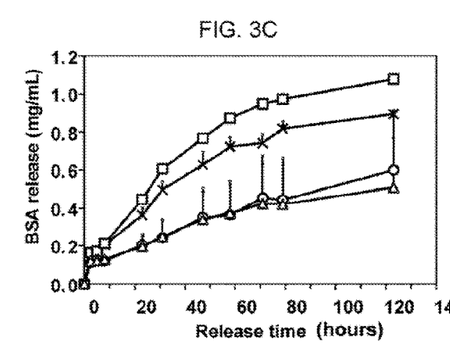
FIG. 3C is a graph showing the effect of vaccine components on cumulative release of BSA protein in various formulations. -X-: BSA/PBS; -□-: BSA/PBS/PEG-b-PLACL/squalene; -○-: BSA/PBS/PEG-b-PLACL/squalene/SPAN®85; -Δ-: BSA/PBS/PEG-b-PLACL/squalene/sorbitan-PLACL 1:4:4.

FIG. 3C shows vaccine components' effects on cumulative release of BSA in various formulations. A fast release was observed in the case of BSA without adjuvant/emulsifier (-X-: BSA/PBS) from which more than 80% of loaded BSA were released into the outside PBS medium within the first 60 hr.

PEG-b-PLACL/squalene emulsion (-□-: BSA/PBS/PEG-b-PLACL/squalene) allows a slight delay at the very beginning, but the protein was quickly released. The PEG-b-PLACL/squalene/SPAN®85 emulsion (-○-: BSA/PBS/PEG-b-PLACL/squalene/SPAN®85) released less than 40% of BSA during the same period of time. Afterwards, the protein release increased continuously and reached an equilibrium (i.e., the BSA concentrations inside and outside the dialysis device were equal). No difference between PEG-b-PLACL/squalene/SPAN®85 (-○-: BSA/PBS/PEG-b-PLACL/squalene/SPAN®85) and PEG-b-PLACL/squalene/sorbitan-PLACL (-Δ-: BSA/PBS/PEG-b-PLACL/squalene/sorbitan-PLACL 1:4:4) formulations was detected over 120 hr. Following the intermediate controlled-release mechanisms, the hydrophilic bioactive agents (or antigens) trapped within the PEG-b-PLACL/sorbitan-PLACL-stabilized emulsion is released mostly by diffusion from the core oil to the surface, but also to a lesser extent by degradation mechanisms and emulsion breaks.

Effects of Vaccine's HLB on Controlled Release

The antigen medium was prepared with a particular concentration of BSA diluted in PBS. 120 mg of PEG-b-PLACL, 240 mg of sorbitan-PLACL conjugates with different HLB values (sorbitan-PLACL with sorbitan:LA:CL being 1:2:2, 1:4:4, 1:8:8 or 1:12:12), 0.68 mL of antigen medium and 0.96 mL of squalene oil were emulsified using a POLYTRON® PT 3100 homogeniser (Kinematica AG, Swiss) under 6,000 rpm for 5 min. In vitro release experiments were performed by using the inverted dialysis tube method, as described above.

Figure 3D:
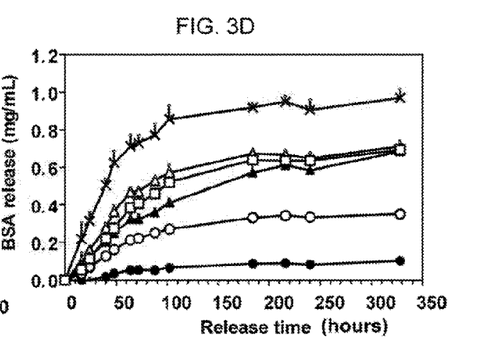
FIG. 3D is a graph showing the effect of hydrophilic-lipophilic balance (HLB) value of the block copolymer in various formulations on BSA release. -X-: BSA/PBS; -Δ-: BSA/PBS/PEG-b-PLACL/squalene/sorbitan-PLACL 1:2:2; -•-: BSA/PBS/PEG-b-PLACL/squalene/sorbitan-PLACL 1:4:4; -○-: BSA/PBS/PEG-b-PLACL/squalene/sorbitan-PLACL 1:8:8; -▲-: BSA/PBS/PEG-b-PLACL/squalene/sorbitan-PLACL 1:12:12; -□-: BSA/PBS/PEG-b-PLACL/squalene/sorbitol-PLACL 1:4:4.

FIG. 3D shows vaccines' HLB effects on cumulative release of BSA in various formulations. A fast release was observed in the case of BSA without emulsion formulation (-X-: BSA/PBS), from which most of loaded BSA was released into the outside PBS medium within the first 100 hr. The sorbitan-PLACL 1:2:2 (-Δ-: BSA/PBS/PEG-b-PLACL/squalene/sorbitan-PLACL 1:2:2), sorbitan-PLACL 1:12:12 (-▲-: BSA/PBS/PEG-b-PLACL/squalene/sorbitan-PLACL 1:12:12), sorbitol-PLACL 1:4:4 (-□-: BSA/PBS/PEG-b-PLACL/squalene/sorbitol-PLACL 1:4:4) emulsions have similar release profiles of free BSA, in which less than 60% of BSA released during the same period of time. Afterwards, protein release increased continuously until it reached a concentration equilibrium between inside and outside of the dialysis device. Oily sorbitan-PLACL 1:4:4 (-•-: BSA/PBS/PEG-b-PLACL/squalene/sorbitan-PLACL 1:4:4) and sorbitan-PLACL 1:8:8 (-○-: BSA/PBS/PEG-b-PLACL/squalene/sorbitan-PLACL 1:8:8) emulsions presented well depot effect to BSA so that hydrophilic BSA was slowly released over 300 hr.

The HLB values for each of the above formulations can be calculated as follows:
"a": the HLB of sorbitan-PLACL 1:2:2=4.0;
"b": the HLB of sorbitan-PLACL 1:4:4=2.2;
"c": the HLB of sorbitan-PLACL 1:8:8=1.2;
"d": the HLB of sorbitan-PLACL 1:12:12=0.8.
"A": The HLB of PEG-b-PLACL=15.

The HLB value of various polysorbasomes are as follows:
PEG-b-PLACL/sorbitan-PLACL 1:2:2=ΣHLB (A+a) =7.7;
PEG-b-PLACL/sorbitan-PLACL 1:4:4=ΣHLB (A+b) =6.5;
PEG-b-PLACL/sorbitan-PLACL 1:8:8=ΣHLB (A+c) =5.8;
PEG-b-PLACL/sorbitan-PLACL 1:12:12=ΣHLB (A+d) =5.5.

One-Pot Synthesis of PEG-b-PLA/Sorbitan-PLA

Figure 4A:
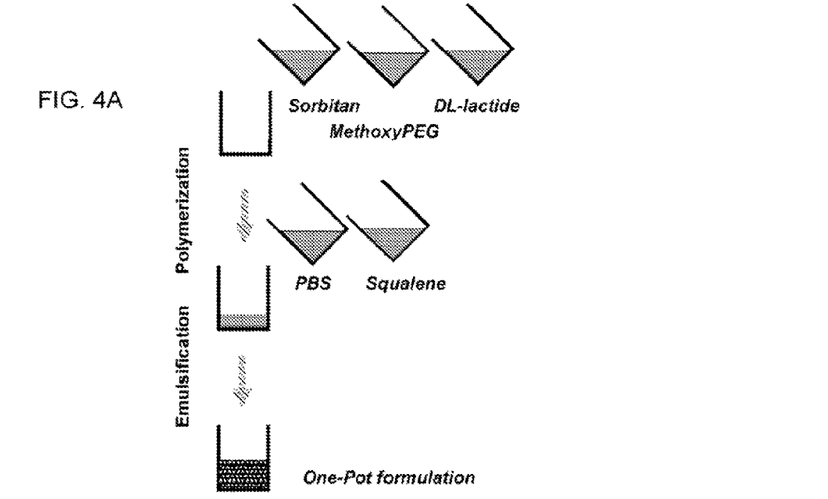
FIG. 4A is a schematic drawing showing one-pot synthesis of PEG-b-PLA and sorbitan-PLA (one-pot formulation).

The invention also relates to preparation of such polymeric conjugates and copolymers in one reactor. This would be much desired because avoiding separation process and purification of intermediate chemical compounds would save time and resources while increasing the chemical yield. Firstly, 0.2 g of sorbitan, 2.8 g of monomethoxy PEG2000, 3 g of DL-lactide, and 30 µL of $SnOct_2$ (catalyst) were introduced into the flask. PEG-b-PLA/sorbitan-PLA mixtures were synthesized by ring-opening polymerization of DL-lactide onto monomethoxy PEG and sorbitan at 140° C. for 24 hr (FIG. 4A). The weight ratios are as follows: sorbitan:monomethoxy PEG:DL-lactide=0.2 g:2.8 g:3.0 g=1:14:15=1:14: (8+7), i.e., 8/15 of lactide would react with sorbitan, and 7/15 of lactide would react with monomethoxy PEG. After the reaction, two products made were sorbitan-polylactide and PEG-polylactide. The weight ratio of sorbitan:lactide in the conjugate sorbitan-polylactide is 1:8, i.e., 1:(4+4). The weight ratio of PEG:lactide in PEG-polylactide is 14:7, i.e., 2:1.

To prepare polysorbasome, 400 mg of the recovery products from above, 0.64 mL of antigen medium, and 0.96 mL of squalene oil were emulsified using a POLYTRON® PT 3100 homogeniser (Kinematica AG, Swiss) under 6,000 rpm for 5 min.

FIG. 4A is a schematic diagram showing synthesis of PEG-b-PLA/sorbitan-PLA and preparation of polysorbasomes. Sorbitan and methoxy PEG were introduced into a reactor, then reacted by polymerization of DL-lactide on sorbitan and methoxy PEG at the same time, resulting a mixture containing sorbitan-PLA conjugate and PEGylated PLA copolymer. Without further purification, the resulting products were dissolved in PBS, mixed with squalene oil, and then homogenized, rendering in an isotropic emulsion.

Figure 4B:
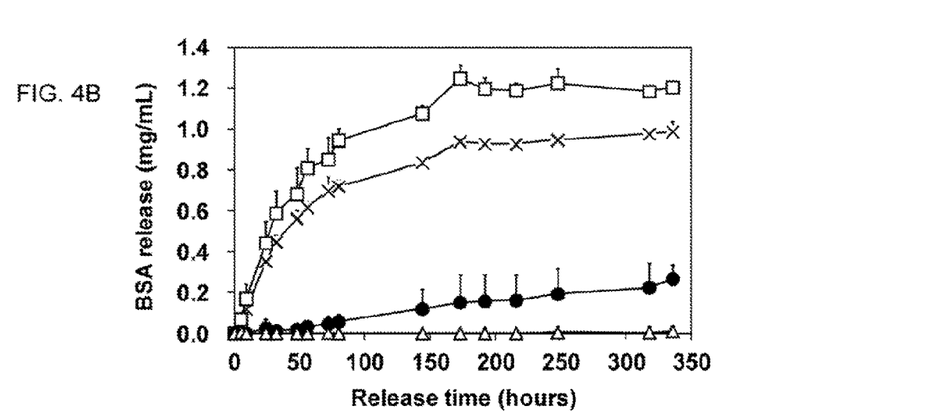
FIG. 4B shows the effect of components on cumulative release of BSA protein in various formulations. -X-: BSA/PBS; -□-: BSA/PBS/PEG-b-PLACL/squalene (O/W); -•-: BSA/PBS/PEG-b-PLA/squalene/sorbitan-PLA (one-pot formulation); -Δ-: BSA/PBS/IFA (W/O).

FIG. 4B shows components' effects on cumulative release of BSA from various one-pot polysorbasome formulations. Similar to PEG-b-PLACL/squalene/sorbitan-PLACL polysorbasome, the hydrophilic BSA protein trapped within the one-pot emulsion was released and the release increased progressively, indicating an intermediate controlled release. -X-: BSA/PBS; -□-: BSA/PBS/PEG-b-PLACL/squalene (O/W); -•-: BSA/PBS/PEG-b-PLA/squalene/sorbitan-PLA (one-pot formulation); -Δ-: BSA/PBS/IFA (W/O). IFA was used for making comparisons because it is a standard for W/O emulsions. It was noted that a PBS/squalene/SPAN emulsion prepared using a similar method was unstable.

Figure 4C:
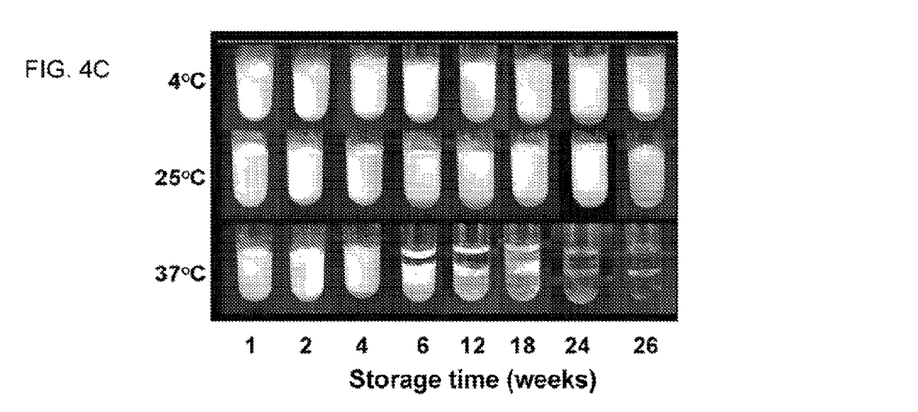
FIG. 4C shows the results of stability test of the BSA/PBS/PEG-b-PLA/squalene/sorbitan-PLA vaccine.

FIG. 4C shows that the emulsions remained stable for about 6 weeks when they were stored at 4° C. and 25° C. Emulsion instability occurred at week-6 under storage at 37° C. This feature confirms that a loss of PLA moiety of the emulsifier PEG-b-PLA/sorbitan-PLA directly affects the stability of the emulsion, leading to emulsion disintegration and squalene/water phase separation.

The stability of PEG-b-PLACL/squalene/sorbitan-PLACL polysorbasome formulation was also tested and the results indicated that it remained stable for more than 10 weeks.

Evaluation of Vaccine Immunity

We investigated whether encapsulating protein antigen into emulsified polysorbasomes would influence antigen-specific immune responses. Polysorbasome-formulated vaccine was prepared by re-dispersing 0.2 mL of stock emulsion into 1.8 mL of aqueous solution and mixed with a test-tube rotator (Labinco LD-79, Netherlands) under 5 rpm at least 1 hr before vaccination.

Six-week old female BALB/c mice were injected intramuscularly (i.m.; 200 µL) with 10 µg of OVA in PBS or formulated with candidate formulations. Serum samples were collected to determine antigen-specific antibody responses by enzyme-linked immunosorbent assay (ELISA).

Figure 5A:
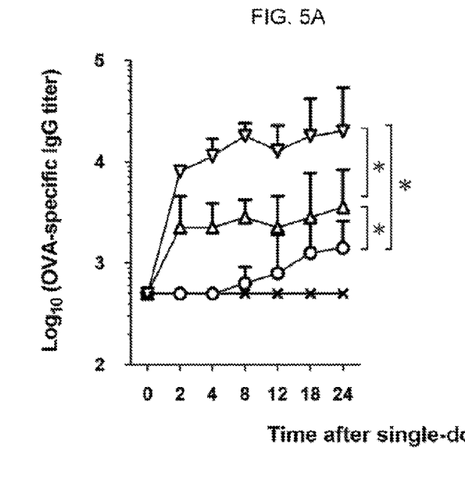
FIGS. 5A-B show the results of evaluations of vaccine immunity via i.m. injection. -X-: PBS control; -○-: OVA/PBS; -Δ-: OVA/PBS/squalene/PEG-b-PLACL/sorbitan-PLACL 1:4:4 (P-1, adsorption); -∇-: OVA/PBS/squalene/PEG-b-PLACL/sorbitan-PLACL 1:4:4 (P-1, encapsulation); -▲-: OVA/PBS/squalene/PEG-b-PLA/sorbitan-PLA (P-2, one-pot formulation, adsorption); -▼-: OVA/PBS/squalene/PEG-b-PLA/sorbitan-PLA (P-2, one-pot formulation, encapsulation). *P<0.05: comparison with non-formulated OVA group at the same time point. OVA means ovalbumin, i.e. albumin from chicken.
Figure 5B:
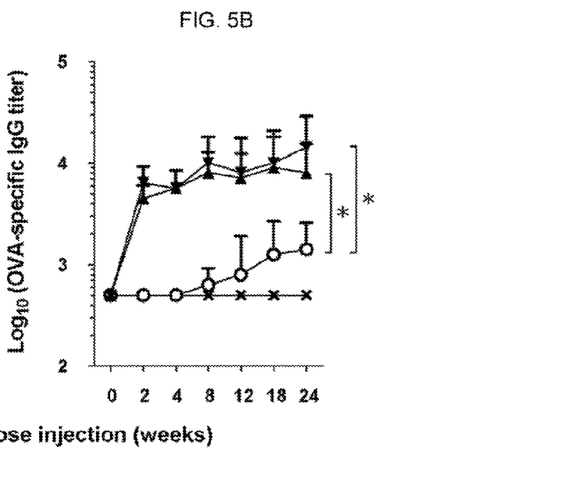

FIGS. 5A-B show the results of evaluations of vaccine immunity via i.m. injection. -X-: PBS control;-○-: OVA/PBS; -Δ-: OVA/PBS/squalene/PEG-b-PLACL/sorbitan-PLACL 1:4:4 (P-1, adsorption); -∇-: OVA/PBS/squalene/PEG-b-PLACL/sorbitan-PLACL 1:4:4 (P-1, encapsulation); -▲-: OVA/PBS/squalene/PEG-b-PLA/sorbitan-PLA (P-2, one-pot formulation, adsorption); -▼-: OVA/PBS/squalene/PEG-b-PLA/sorbitan-PLA (P-2, one-pot formulation, encapsulation). *P<0.05: comparison with non-formulated OVA group at the same time point. OVA means ovalbumin, i.e. albumin from chicken.

FIG. 5A shows the anti-OVA IgG antibody titers measured in the animal groups after a single injection with PBS. OVA/PBS, P1 (OVA/PBS/squalene/PEG-b-PLACL/sorbitan-PLACL 1:4:4) adsorption (-Δ-), and encapsulation formulations (-∇-), respectively. The antibody titer elicited by the non-adjuvanted OVA/PBS formulation (-○-) was barely detected at week-8. When the antigen was adsorbed (-Δ-) and/or encapsulated (-∇-) in a Sorbitan-PLACL/PEG-b-PLACL emulsion, antibody titers were enhanced significantly. In this emulsion, antigen encapsulation (-∇-) induced a higher antibody titer than antigen adsorption (FIG. 5A: -∇- vs. -Δ-, p<0.05).

FIG. 5B shows the anti-OVA IgG antibody titers measured in the animal groups after a single injection with PBS, OVA/PBS, P2 (OVA/PBS/squalene/PEG-b-PLA/sorbitan-PLA 1:4:4) adsorption (-▲-), and encapsulation formulations (-▼-), respectively. The antibody titer elicited by the non-adjuvanted OVA/PBS formulation (-○-) was barely detected at week-8. When the antigen was adsorbed (-▲-) and/or encapsulated (-▼-) in a Sorbitan-PLA/PEG-b-PLA emulsion, antibody titers were enhanced significantly. The PEG-b-PLA/sorbitan-PLA emulsion can be prepared by one-pot synthesis. In this emulsion, antigen encapsulation (-▼-) or adsorption (-▲-) induced the same amount of antibody titers, which is unlike the emulsion PEG-b-PLACL/sorbitan-PLACL shown in FIG. 5A.

Figure 6A:
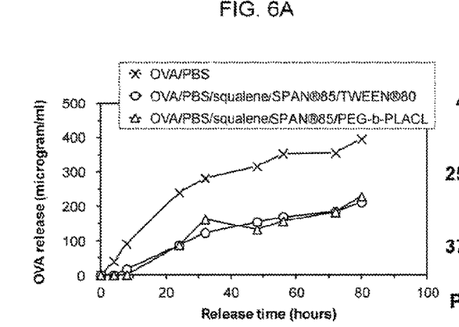
FIG. 6A shows controlled release of an antigen (ovalbumin) in various formulations.

FIG. 6A shows in vitro controlled release of an antigen (OVA) in various formulations at 37° C. In the OVA/PBS formulation without emulsifiers, protein release continuously increased over 80 hrs until an equilibrium concentration of inside and outside dialysis device was reached. In the SPAN® 85/PEG-b-PLACL stabilized emulsion, a different controlled-release profiles was observed. The OVA trapped within the SPAN® 85/PEG-b-PLACL-stabilized emulsion was released probably by diffusion from the core oil to the surface, exhibiting the same controlled release effect as a traditional W/O/W emulsion comprising SPAN® 85 and TWEEN® 80.

U.S. Pat. No. 8,444,993 was the first in disclosing concepts of "stable" and "degradable" vaccine emulsions. It discloses amphiphilic degradable polymers as a hydrophilic emulsifier that stabilizes aqueous/oily interfaces to afford an emulsion with oil droplets dispersed in an aqueous solution. The stable nature of the polymeric emulsifier allows to stabilize the emulsion during preparation and storage, and the degradable nature permits to destroy the emulsion and further to be absorbed post-administration.

Figure 6B:
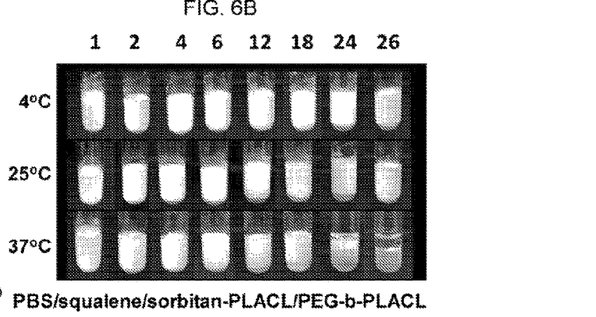
FIG. 6B shows the stability of W/O/W emulsions comprising emulsifiers Sorbitan-PLACL/PEG-PLACL at various temperature during the 26-week period.
Figure 6C:
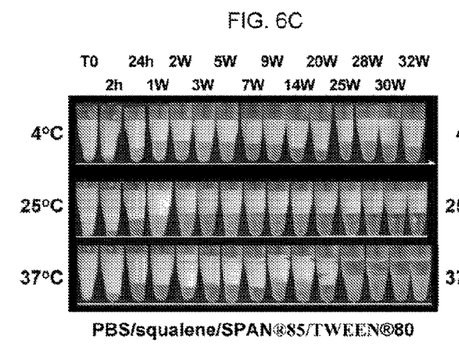
FIGS. 6C-D show the stability of W/O/W emulsions comprising emulsifiers SPAN/®TWEEN® and SPAN®/PEG-PLACL, respectively, at various temperature during the 32-week period.
Figure 6D:
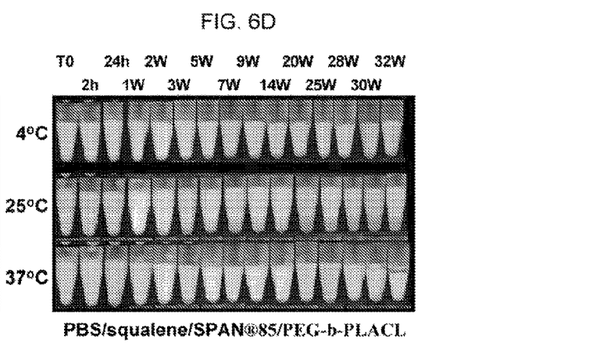

FIGS. 6B-D show the stability of emulsions stored at various temperatures, 4° C., 25° C. and 37° C., which mimics cold chain, ambient, and extreme storage conditions. The 37° C. was selected to mimic post-administration stage.

The SPAN® 85/TWEEN-stabilized emulsion after homogenization was perfectly milky white and isotropic from top to bottom (FIG. 6C). This emulsion was stable, no oil phase being dissociated while storage at 4° C. or 25° C. for the 32-week observation period. Even though about 20% of water disassociated at the bottom of the vial was observed at 24 hours at 4° C. or 25° C., the emulsion could be easily re-formed by simply vortex mixing. When being stored at 37° C., 20% of free oil dissociated from the emulsion starting at week 2. The Oil phase and water phase completely separated at week 25 with the oil phase staying at the top layer and water phase at the bottom layer (FIG. 6C). Once oil/water phase separated, the emulsion could no longer be re-formed by simply vortex mixing. This emulsion system is not an ideal vaccine formulation for those tropical regions where may have difficulties in storage of this emulsion at low temperatures and keeping it stable.

Replacing TWEEN with PEG-b-PLACL significantly enhanced the stability of the emulsion (FIG. 6D). This formulation was very stable even at 37° C. for at least 28 weeks because no oil phase dissociation was observed until week 30, when it was observed that about 10% of free oil dissociated from the emulsion and stayed at the top layer in the vial. Only slight water dissociation was observed during the entire 32-week observation period, and the water dissociation was much less than that in the SPAN® 85/TWEEN-stabilized emulsion. This indicated that the SPAN/PEG-b-PLACL emulsion can avoid refrigeration storage since it is very stable even at 37° C. for at least 28 weeks.

By contrast, replacing SPAN/PEG-b-PLACL with Sorbitan-PLACL/PEG-b-PLACL significantly decreased the stability of the emulsion at 37° C. The Sorbitan-PLACL/PEG-b-PLACL W/O/W emulsion was less stable at 37° C. than the SPAN/PEG-b-PLACL emulsion because it exhibited oil phase dissociation at 37° C. at least 4 weeks earlier, i.e., 30% of oil dissociation at week-24, even though at 4° C. and 25° C. this emulsion was as stable as that of the SPAN/PEG-b-PLACL emulsion (FIG. 6B). Once an oil dissociation from the emulsion started the oil/water phase separation was quickly completed by week-26, exhibiting two layers with the oil staying at the top and the water at the bottom of the vial (FIG. 6B). This feature confirms that the degradation of the PLACL moiety in the Sorbitan-PLACL emulsifier directly affected the stability of the Sorbitan-PLACL/PEG-b-PLACL-stabilized emulsion, leading to emulsion disintegration and oil/water phase separation. The data indicated that an oil/water interface stabilized by the Sorbitan-PLACL/PEG-b-PLACL not only can provide high stability to vaccine antigens carried by emulsified particles during preparation and storage, but also afford high degradability and absorbability in vivo. These technical features are significant and important to vaccine development as emulsions possessing high degradability and absorbability at 37° C. is important for vaccine safety and efficacy.

A composition in a W/O/W emulsion according to the invention have the following advantages: (I) free of the traditional emulsifiers SPAN®, TWEEN®, and poloxamers, which may cause toxicities; (II) emulsion stability and long shelf-storage life; (III) readily degradable and bioabsorbable at 37° C.

The foregoing description of the exemplary embodiments of the invention has been presented only for the purposes of illustration and description and is not intended to be exhaustive or to limit the invention to the precise forms disclosed. Many modifications and variations are possible in light of the above teaching. The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope.

All references cited and discussed in this specification are incorporated herein by reference in their entireties and to the same extent as if each reference was individually incorporated by reference.

What is claimed is:

1. A water-in-oil-in-water (W/O/W) emulsion comprising:

(a) a continuous aqueous phase, comprising $H_2O$; and (b) an oil phase or an oil shell, dispersed in the continuous aqueous phase, the oil phase or the oil shell comprising:

(i) oil;

(ii) an internal aqueous phase, dispersed within the oil phase or the oil shell; and (iii) a lipophilic sorbitan-polyester conjugate, stabilizing an interface between the oil and the inner aqueous phase to form a water-in-oil (W/O) emulsion, the lipophilic sorbitan-polyester conjugate comprising:

(1) sorbitan; and (2) poly(lacetide-co-ε-caprolactone) or polylactic acid (polylactide), conjugated to the sorbitan: and (c) a hydrophilic polymer, stabilizing an interface between the continuous aqueous phase and the oil phase or the oil shell to form an oil-in-water (O/W) emulsion.

2. The emulsion of claim 1, wherein the weight ratio of sorbitan: lactide: caprolactone in the sorbitan-poly(lactide-co-ε-caprolactone) conjugate is greater than 1: 2: 2 but less than 1: 12: 12.

3. The emulsion of claim 2, wherein the weight ratio of sorbitan: lactide: caprolactone in the sorbitan- poly(lactide-co-ε-caprolactone) conjugate ranges from 1: 3: 3 to 1: 8: 8.

4. The emulsion of claim 1, wherein the hydrophilic polymer is selected from the group consisting of poly (ethylene glycol)-block-poly (lactide-co-ε-caprolactone) and poly(ethylene glycol)-block-polylactide.

5. The emulsion of claim 1, wherein
(i) the continuous aqueous phase or the inner aqueous phase comprises an antigen or an additional bioactive agent;
(ii) the continuous aqueous phase or the inner aqueous phase comprises both an antigen and an additional bioactive agent;
(iii) the continuous aqueous phase comprises an antigen and the inner aqueous phase comprises an additional bioactive agent; or
(iv) the continuous aqueous phase comprises an additional bioactive agent and the inner aqueous phase comprises an antigen.

6. The emulsion of claim 5, wherein the additional bioactive agent is an immunostimmulant.

7. The emulsion of claim 1, which is free of sorbitan esters, sorbitan ethoxylates, esters of fatty acids and hexitol anhydrides, marmide monooleate and poloxamers.

8. The emulsion of claim 1, wherein the water-in-oil-in-water emulsion exhibits particles having a size ranging from 400 to 600 nm.

9. The emulsion of claim 2, which is free of sorbitan esters, sorbitan ethoxylates, esters of fatty acids and hexitol anhydrides, mannide monooleate and poloxamers.

10. The emulsion of claim 3, which is free of sorbitan esters, sorbitan ethoxylates, esters of fatty acids and hexitol anhydrides, mannide monooleate and poloxamers.

11. The emulsion of claim 4, which is free of sorbitan esters, sorbitan ethoxylates, esters of fatty acids and hexitol anhydrides, mannide monooleatea and poloxamers.

12. The emulsion of claim 6, which is free of sorbitan esters, sorbitan ethoxylates, esters of fatty acids and hexitol anhydrides, mannide monooleate and poloxamers.

13. A method of preparing the water in oil in water (W/O/W) emulsion of claim 1,
(I) the method comprising:
(a) introducing sorbitan, monomethoxy polyethylene glycol, and DL-lactide into a reactor;
(b) performing a polymerization of the DL-lactide on the sorbitan and the monomethoxy polyethylene glycol in the presence of a catalyst to of a mixture containing sorbitan-polylactide conjugate and poly(ethylene glycol)-block-polylactide;
(c) adding a first aqueous solution into the mixture containing the sorbitan-polylactide conjugate and the poly(ethylene glycol)-block-polylactide to obtain a first aqueous mixture;
(d) adding oil into the first aqueous mixture to obtain an aqueous oil mixture; and
(e) homogenizing the aqueous oil mixture to afford the W/O/W emulsion of claim 1;
or (II) the method comprising:
(i) admixing sorbitan-polyester conjugate, poly(ethylene glycol)-block-poly(lactide-co-ε-caprolactone), and a first aqueous solution to obtain a first aqueous mixture;
(ii) adding oil into the first aqueous mixture to obtain an aqueous oil mixture; and
(iii) homogenizing the aqueous oil mixture to afford the W/O/W emulsion of claim 1.

14. The method of claim 13, prior to step (i) further comprising:
(1) admixing sorbitan with DL-lactide andε-caprolactone; and
(2) performing a polymerization reaction of the DL-lactide and the ε-caprolactone on the sorbitan to afford the sorbitan-polyester conjugate.

15. The method of clam 14, wherein prior to step (1) the method further comprises providing sorbitol and performing an anhydrization reaction of the sorbitol in the presence of phosphoric acid to afford the sorbitan.

16. The method of claim 13, wherein the first aqueous solution in step (c) or (i) comprises an antigen or a bioactive agent to afford the W/O/W emulsion having the antigen or the bioactive agent encapsulated within the oil phase or the oil shell.

17. The method of claim 13, after step (e) in (I) or after step (iii) in (II) further comprising the steps of:
adding a second aqueous solution comprising an antigen or an additional bioactive agent into W/O/W emulsion from step (e) or step (iii) to obtain a second mixture with the proviso that the first aqueous solution does not comprise the antigen or the additional bioactive agent; and
dispersing the second mixture to afford a W/O/W emulsion having the antigen or the additional bioactive agent adsorbed onto surface of the oil phase or on the oil shell.

18. The method of claim 16, wherein the bioactive agent is an immunostimulant.

19. A method for enhancing a response to an immunogen, or for delivering an inmunogen or a bioactive agent into a body in a subject in need thereof, comprising:
administering to the subject in need thereof the emulsion of claim 1, wherein the immunogen or bioactive agent is present in the emulsion.

20. The method of claim 17, wherein the bioactive agent is an immunostimulant.

* * * * *